United States Patent [19]

Geber

[11] Patent Number: 5,100,878
[45] Date of Patent: Mar. 31, 1992

[54] BLOCKING THE EFFECT OF TERATOGENS ON A FETUS

[75] Inventor: William F. Geber, Augusta, Ga.

[73] Assignee: American Maize-Products Company, Stamford, Conn.

[21] Appl. No.: 519,833

[22] Filed: May 7, 1990

[51] Int. Cl.$^5$ .......................................... A61K 31/715
[52] U.S. Cl. .................................................... 514/58
[58] Field of Search .................. 514/58; 536/121, 103, 536/112

[56] References Cited

U.S. PATENT DOCUMENTS

| | | | |
|---|---|---|---|
| 2,923,704 | 2/1960 | Berger | 536/121 |
| 4,020,160 | 4/1977 | Bernstein et al. | 514/58 |
| 4,066,829 | 3/1978 | Nair et al. | 536/103 |
| 4,258,180 | 3/1981 | Lewis et al. | 536/112 |

OTHER PUBLICATIONS

Chemical Abstracts (92: 105205y) 1980.
J. Szejtli and G. Sebestyen, "Resorption, Metabolism and Toxicity Studies on the Peroral Application of beta-Cyclodextrin", Starch/Starke, 31, Nr. 11 (1979), pp. 385–389.
Chang et al., Dextran Sulfate as an Inhibitor against the Human Immunodeficiency Virus; Proceedings of the Society for Experimental Biology and Medicine 189, 304–309; Jul. 21, 1988.
Gerber; anti-Viral Compounds as Anti-Teratogens; Teratology-The Internation Journal of Abnormal Development; vol. 29, No. 2; Apr. 1984.
Folkman et al., Control of Angiogenesis with Synthetic Heparin Substitutes; vol. 243, pp. 1490–1493; Dec. 1988.
Beyer; A Study of Pharmacological Protection of Drug Induced Teratogenesis in the Fetal Hamster; Jun. 1984.

Primary Examiner—Frederick E. Waddell
Assistant Examiner—K. Weddington
Attorney, Agent, or Firm—Lucas & Just

[57] ABSTRACT

By administration of sulfated cyclodextrin on a pregnant mother, the effect of a teratogen on a developing fetus is blocked. Blocking the effect of the teratogen reduces congenital defects in a developing fetus. The sulfated cyclodextrin has also been found to reduce the effect of the teratogen on a host. The sulfated cyclodextrin is administered either before or after onset of organogenesis and either before or after exposure to the teratogen. Teratogens include radiation, temperature extremes, chemicals, drugs, bacteria, viruses, hormones, stress, injury, pregnancy, and fatigue.

10 Claims, No Drawings

BLOCKING THE EFFECT OF TERATOGENS ON A FETUS

This invention relates to a method for blocking the effect of a teratogen on a fetus by administration of a sulfated cyclodextrin to a pregnant mother. Blocking the effect of teratogens with sulfated cyclodextrin prevents congenital birth defects in some cases and in other cases reduces the effect of the teratogen on the fetus.

Congenital birth defects are defects which originated in an organism during development in the uterus and which are not necessarily due to heredity.

Teratogens include radiation, temperature extremes, chemicals, drugs, bacteria, viruses, hormones, stress, injury, pregnancy, and fatigue. Teratogens affect the developing organism in a pathological sense and can result in congenital defects such as prenatal defects, structural defects, functional defects, behavioral defects, or an increased likelihood of cancer.

Prenatal defects occur in over 45% of conceptions. Over 30% of these defects are manifested before implantation of the embryo in the uterus and result in reabsorption of the embryo without further development. Approximately 15% of prenatal defects result in spontaneous miscarriage.

Structural defects occur in approximately 3% of viable births. Structural defects are visible abnormalities in the structure of the fetus at birth.

Functional defects occur in an additional approximately 7% of births. Functional defects do not manifest themselves until some period after birth wherein a system does not perform its function, e.g. a learning disability which is generally not detectable at birth.

Additionally, another 20% of births involve infants with behavioral defects which are caused by an in utero induced abnormality. These defects are also generally only discovered later in life and are not apparent in the newborn infant.

A higher likelihood of cancer is another congenital birth defect which may result from in utero exposure to an oncogenic agent. About 80-85% of cancers are induced by the genetic and congenital makeup of the organism and may be triggered by one or more oncogenic agents, or a combination thereof. Oncogenic agents and teratogens are in many instances the same.

It is known that teratogens cause birth defects. However it is not known if the teratogen affects the mother, the fetus, or both. It is also not known how the teratogen causes the congenital birth defect. It is believed that one possible point of damage by teratogens is the interferon component of the immune system of the fetus. Interferon is a low molecular weight protein that is produced by cells. It has been found that a wide range of teratogens decrease the amount of interferon or inhibit the production of interferon in cells of the fetus. The immune system of a cell, and specifically interferon, is thought to function together with the genetic material of the cell to modify, control and protect the genetic mechanisms which direct cellular activities. Thus, the genetic material of each cell is made susceptible to damage by the teratogen that damaged the immune system.

Previous methods for blocking the effect of teratogens on a fetus to reduce congenital defects include pre- or post-teratogen exposure administration of an agent such as tilorone hydrochloride ("tilorone 1"; 2,7-bis [2-diethylamino ethoxy]-fluoren-9-one; the bis basic ether of fluorene), dextran sulfate (a highly sulfated polysaccharide), amantadine hydrochloride (1-adamantanamine hydrochloride), polyinosinic: polycytidylic acid (Poly I:C; a double-stranded, polyribonucleotide complex), and RMI 11,567 DA ("tilorone 2"; the bis basic ketone of dibenzofuran). These agents are sometimes referred to as antiteratogens, and have all been found to lower the likelihood of central nervous system lesions which result in exencephaly in an organism; however, a higher frequency of congenital defects in the urogenital system occurs. In addition, only limited specific activity has been found for any of these compounds directed towards a specific defect and none of these compounds universally block a broad rang of defects.

Dextran sulfate has additionally been found to have some anti-viral activity on a narrow range of viruses, see R. Shihman Chang et al., "Dextran Sulfate as an Inhibitor Against the Human Immunodeficiency Virus", *Proceedings of the Society for Experimental Biology and Medicine*, 189, 304-309 (1988).

Sulfated cyclodextrins are known and have been used for treatment of diseases. Specifically, U.S. Pat. No. 2,923,704 teaches cyclohexaamylose sulfate and cycloheptaamylose sulfate for treatment of coronary disease. Cyclodextrin sulfates are also known to have anti-inflammatory, fatty serum clarifier and anti-artiosclerotic activity, see Japanese Patent No. 75/36422 (CA, 83:79544a). U.S. Pat. Nos. 4,020,160 and 4,258,180 teach that cyclodextrin and modified cyclodextrin sulfate salts inhibit complement activity in body fluids. Beta cyclodextrin tetradecasulfate, when administered with a steroid, has been shown to inhibit angiogenesis, see J. Folkman et al., "Control of Angiogenesis with Synthetic Heparin Substitutes", *Science*, 243, 1490-1493 (Mar. 17, 1989).

It has now been discovered that the effect of a teratogen on a fetus is blocked by the administration of an effective amount of a sulfated cyclodextrin to the mother in either a prophylactic or therapeutic manner. Because the effect of the teratogen is blocked, congenital birth defects in the fetus are reduced. It has also been discovered that, where the effect of the teratogen is not fully blocked, its effect on the fetus is reduced by the administration of an effective amount of sulfated cyclodextrin. For example, where the effect of a teratogen on the fetus is reduced birth weight, the administration of sulfated cyclodextrin to the mother having the teratogen in her system will result in a fetus with a less reduced birth weight.

The term "fetus" as used in the specification and claims means any prenatal organism between conception and birth which is normally developed in utero. This definition includes a prenatal organism which is first conceived in vitro and later implanted in a uterus. The term "fetus" includes the term "embryo".

The exact mechanism of the present invention is not known, however, it is thought that the sulfated cyclodextrin blocks the effect of a teratogen by stimulating production or release of interferon which, in turn, directly blocks the teratogenic activation on the genetic material of the developing fetus.

Sulfated cyclodextrin has many advantages over other known antiteratogens. For example, sulfated cyclodextrin is a simple and easily synthesized substance; it has a lower toxicity as compared to other antiteratogenic substances; and use of the sulfated cyclodextrin causes less undesirable side effects. Other antiteratogens are usually nucleoside derivatives of teratogenic substances which are difficult to synthesize and which cause undesirable side effects.

In accordance with the present invention, sulfated cyclodextrin is used as an antiteratogen in either a prophylactic or a therapeutic manner. Administration of sulfated cyclodextrin before exposure to a teratogen provides a prophylactic effect; administration after exposure provides a therapeutic effect. The sulfated cyclodextrin may also be administered to a potential mother before conception.

Preferably, the sulfated cyclodextrin is administered during the gestation period of organogenesis. Of course, depending on the species, organogenesis occurs at different times during the gestation period. For hamsters, the most critical phase of organogenesis occurs about 8-9 days after conception; for humans, the most critical phase of organogenesis occur about 3-9 weeks after conception. It is appropriate to continue to administer the sulfated cyclodextrin throughout the pregnancy and after birth if lactating.

The sulfated cyclodextrin is administered to the female by any pharmaceutically acceptable method. Acceptable administration methods include oral administration; and sub-cutaneous (SC), interperitoneal (IP), or intravenous (IV) injection. Administration of the sulfated cyclodextrin is made by using any pharmaceutically acceptable carrier or diluent.

A range of doses may be employed depending on the mode of administration, the species of the host, and the pharmaceutical carrier. Determination of an effective amount for a specific host is conventional. The dosage range is adjusted to provide optimum preventative or therapeutic response in the warm-blooded animal being treated. In general, the amount of compound administered can vary over a wide range to provide from about 5 mg/kg to about 200 mg of sulfated cyclodextrin per kilogram body weight of animal per day.

In preventative or therapeutic use the sulfated cyclodextrin as used in the present invention is administered in the form of a conventional pharmaceutical composition. Such a composition is formulated so as to be suitable for oral or parenteral administration. The sulfated cyclodextrin is combined with a pharmaceutically acceptable carrier which takes a wide variety of forms depending on the form of administration, such as liquid or tablet form.

To make a tablet, the sulfated cyclodextrin is mixed with conventional tabletting ingredients such as corn starch, lactose, sucrose, sorbitol, talc, stearic acid, magnesium stearate, dicalcium phosphate, gums, or similar materials as non-toxic pharmaceutically acceptable carriers or diluents and formed into a tablet. The tablets or pills can be laminated or otherwise compounded to provide a dosage form affording the advantage of prolonged or delayed action or predetermined successive action of the enclosed medication. For example, the tablet or pill can comprise inner dosage and outer dosage components, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids or mixtures of polymeric acids with such materials as shellac, shellac and cetyl alcohol, cellulose acetate and the like. A particularly advantageous enteric coating comprises a styrene maleic acid copolymer together with known materials contributing to the enteric properties of the coating. The tablet or pill may be colored through the use of an appropriate non-toxic dye, so as to provide a pleasing appearance.

In liquid form, the sulfated cyclodextrin is in a sterile suspension or solution for parenteral use. Sulfated cyclodextrin is a solid at room temperature. Isotonic preparations containing suitable preservatives are also desirable for injection use.

The term "dosage" a used herein refers to physically discrete units suitable as a unitary dosage for warm-blooded animal subjects, each unit containing a predetermined quantity of active component calculated to produce the desired preventative or therapeutic effect in association with the required pharmaceutical diluent, carrier or vehicle.

Good results have been found using a sulfated cyclodextrin in the sodium salt form (monovalent). However, any pharmaceutically acceptable salt form of the sulfated cyclodextrin can be used in accordance with the present invention.

A dosage of 50-90 mg/kg has been found to be effective for preventative treatment in hamsters. An effective amount of the sulfated cyclodextrin to reduce the effect of congenital defects in warm-blooded animals is from about 5 mg/kg to about 200 mg/kg.

A suitable method for making the sulfated cyclodextrin of the present invention is by mixing the cyclodextrin and the sulfating agent in a solvent such as dimethylformamide, hexamethylphosphoramide or dimethylsulfoxide, heating the mix to between about 40° to about 80° C. and holding the mix at that temperature for about 12 to 30 hours, preferably under vigorous agitation. Suitable sulfating agents include trimethylammonium sulfur trioxide, pyridinium sulfur trioxide, and chlorosulfonic acid. The product is then recovered in a conventional manner.

Alpha, beta or gamma cyclodextrin is used to make the sulfated cyclodextrin of the present invention; however, best results have been found using beta cyclodextrin.

Cyclodextrins are also called "Schardinger dextrins" and are cyclic oligosaccharides composed of anhydroglucose groups bonded together by alpha 1,4 bonds. The six-membered ring structure is called alpha cyclodextrin, the seven-membered ring is beta cyclodextrin and the eight-membered ring is gamma cyclodextrin. The cyclodextrins have different chemical and physical properties than the linear oligosaccharides derived from starch in that they are non-reducing dextrins. The ring structure of the cyclodextrin molecule is used as a host for the inclusion of various compounds, usually organic, for the food, pharmaceutical and chemical fields.

As is also well-known, cyclodextrins are produced from starch of any selected plant variety such as corn, potato, waxy maize and the like which may be modified or unmodified starch derived from cereal or tuber origin and the amylose or amylopectin fractions thereof. The selected starch, in aqueous slurry at selected concentrations up to about 35% by weight solids, is usually liquefied by treatment with a liquefying enzyme such as bacterial alpha-amylase enzyme and then subjected to a treatment with a transglycosylase (CGT) enzyme to form the cyclodextrins.

The amount of the individual alpha, beta and gamma cyclodextrins produced by treating the starch with CGT will vary depending on the selected starch, selected CGT and processing conditions. The parameters to select for the CGT conversion for the desired result in the amount of each individual cyclodextrin to be produced is conventional and well-described in the literature.

Separation of the alpha, beta and gamma cyclodextrins is also conventional. The chromatographic column disclosed in U.S. Pat. No. 4,808,232 dated Feb. 28, 1989 has been found to be effective for the separation of the different types of cyclodextrins.

The molecular ratio of sulfating agent to the number of hydroxyl groups on the cyclodextrin determines the degree of sulfation. A degree of substitution (DS) of the sulfate on the cyclodextrin of about 1–3 has been found to produce good results. Best results have been obtained with a DS of 2. Degree of substitution is the average of the number of hydroxyl groups on an anhydroglucose replaced with sulfate groups.

It will be understood that the sulfated cyclodextrin as used in the present invention may be modified by adding other groups to the cyclodextrin which have antiteratogen activity. Such antiteratogenic groups include, but are not limited to, all or part of the ascorbic acid molecule, all or part of the salicylate molecule, and all or part of the naloxone molecule. Additionally, the sulfated cyclodextrin can be combined with other antiteratogens when administered to a host.

These and other aspects of the present invention may be more fully understood with reference to the following examples.

GENERAL EXPLANATION OF EXAMPLES

In all of the examples, timed pregnant Harlan Sprague Dawley outbred hamsters were injected (SC or IP) with a teratogen on day 8 of gestation during the hours of 9 to 11, which is approximately the beginning of the organogenesis period of gestation. When using the prophylactic method of treatment of the present invention, about 15–60 minutes before injection of the teratogen, the hamsters were injected with sulfated cyclodextrin. When using the therapeutic method of treatment of the present invention, about 15–60 minutes after injection of the teratogen, the hamsters were injected with sulfated cyclodextrin. Control sets of hamsters received an injection of saline, carboxyl methyl cellulose (CMC) solution, or sulfated cyclodextrin only. The amount of each injection is shown in units of mg/kg which means milligram of compound injected per kilogram of host, i.e. mother plus fetus.

After injections of the pregnant hamster on day 8, the animal was returned to its cage and left undisturbed under normal laboratory conditions, with food and water supplied ad libitum. On day 15, when the mother was near birth, the mother was sacrificed by an overdose of ether, the fetuses removed, examined, and placed in Bouins solution for further examination. The presence of defective fetuses was determined by detailed morphological dissection of each fetus.

The value for the weight of the mother after birth of the litter which is listed in the tables of the examples is the weight of the mother including the placenta.

Comparisons were made between the saline or CMC injected groups and the teratogen injected groups to determine the effectiveness of the sulfated cyclodextrin and the results are reported in the following examples. Depending on the teratogen used, blocking of defects using the present invention occurred in about 20–96% of the fetuses born, as compared to fetuses without treatment. The defect blocking value is determined in the following manner:

The total number of defective fetuses of the group of females exposed only to the teratogen is divided by the total number of fetuses in that same group. This number is multiplied by 100 to get the number M.

Next, the total number of defective fetuses of the group of females exposed to both the teratogen and the sulfated cyclodextrin is divided by the total number of fetuses in that same group. This number is multiplied by 100 to obtain the number $M^*$.

The blocking value is obtained by the following formula:

$$\text{Blocking Value} = [(M^*/M - 1)](-100\%)$$

The sulfated cyclodextrin used in the examples was beta-cyclodextrin tetradecasulfate. It was prepared by dissolving 5.0 g of beta cyclodextrin (4.4 moles) in 250 ml dimethylformamide (DMF). To this was added 15.0 g of trimethylammonium sulfur trioxide ($SO_3N(CH_3)_3$) (25 equiv.). The mix was then heated to 70° C. and vigorously stirred for 24 hours while the temperature was maintained. It was then cooled to room temperature and the DMF layer was decanted off. The residue was dissolved in 250 ml water and 75 ml of 30% sodium acetate was added. This new mixture was stirred vigorously for 4 hours and was then poured into 4000 ml ethanol and allowed to stand overnight to form a solid. The solid was filtered, recrystallized and washed with absolute ethanol and with diethyl ether. Dry product was produced over phosphorus pentoxide ($P_2O_5$) in vacuo and 10.3 g of product was recovered having a DS of 2.

The types of congenital defects observed were:
a) exencephaly/ancephaly;
b) myelocele
c) cranioschisis;
d) spina bifida;
e) anasarca;
f) gastroschisis (omphalocele);
g) runt—fetus that is at least 40–50% smaller than rest of litter which may or may not also have a defect. The fetus being a runt was only calculated as a defect when the runt was more than 50% smaller than the fetuses of the rest of the litter;
h) microcephalic.

These defects are noted in each table in the examples and are referred to by the letter corresponding to the defect in the above list, preceded by the number of fetuses exhibited the defect, e.g. 4a means 4 fetuses exhibited exencephaly.

The defects are based on the number of defective fetuses per litter. Although some individual fetuses in a litter may contain multiple defects, the fetus is counted only once as defective, and the multiple defects merely noted in the table.

Where a fetus had multiple defects, the individual fetus will be shown in the tables with both letters, e.g. 1ab means that one fetus had both exencephaly and myelocele.

The control data for the subsequent examples are listed below in Table A.

TABLE A

| Control Agent | Total Litters | Average Weight of Hamster at Injection (g) | Average Weight of Hamster at Birth (g) | Number of live Fetuses | Fetuses/ Litter (Avg.) | Defects |
|---|---|---|---|---|---|---|
| Saline (0.9% NaCl) 0.5 ml/hamster | 20 | 133 | 127 | 220 | 11.0 | 0 |
| Carboxyl methyl cellulose (CMC) (0.25% CMC) 0.5 ml/hamster | 15 | 124 | 120 | 174 | 11.6 | 0 |
| Sulfated Beta Cyclodextrin (50 mg/kg) 0.5 ml/hamster | 20 | 128 | 124 | 228 | 11.4 | 0 |

EXAMPLE 1

Teratogen: Acetazolamide (AZM)
Concentration: 3000 mg/20 ml saline
Method of Injection: IP
Dosage: 1500 mg/kg
Blocking Agent: Sulfated beta cyclodextrin
Concentration: 115 mg/12 ml saline
Method of Injection: IP
Dosage: 70 mg/kg The hamsters were injected with sulfated beta cyclodextrin 50 minutes before injection of the acetazolamide.

The results of injection of acetazolamide alone are reported in Table 1 as follows; the results of acetazolamide and sulfated beta cyclodextrin are reported in Table 2.

TABLE 1

| Sample No. | Weight of Hamster at Injection (g) | Weight of Hamster After Birth (g) | # Live Fetuses | Defects |
|---|---|---|---|---|
| 1 | 140 | 120 | 10 | 2-3 g |
| 2 | 122 | 120 | Not Pregnant | |
| 3 | 118 | 118 | Not Pregnant | |
| 4 | 134 | 122 | 8 | 4a, 1b |
| 5 | 118 | 115 | 8 | 2a, 1b |

Average Number of Fetuses/Litter: 8.7
Average Weight of Mother at Injection: 131 g
Average Weight of Mother After Birth: 119 g
M: 31% [(8/26)(100%)]

TABLE 2

| Sample No. | Weight of Hamster at Injection (g) | Weight of Hamster After Birth (g) | # Live Fetuses | Defects |
|---|---|---|---|---|
| 1 | 136 | 129 | 6 | 0 |
| 2 | 136 | 117 | Not Pregnant | |
| 3 | 140 | 127 | 11 | 0 |
| 4 | 134 | 122 | 7 | 0 |
| 5 | 142 | 130 | 8 | 1b |

Average Number of Fetuses/Litter: 8.0
Average Weight of Mother at Injection: 138 g
Average Weight of Mother After Birth: 127 g
M*: 3% [(1/32)](100%)
Blocking Value: 90% [(3/31)−1] (−100%)

EXAMPLE 2

Teratogen: Acetazolamide (AZM)
Concentration: 4500 mg/30 ml CMC
Method of Injection: IP
Dosage: 1500 mg/kg
Blocking Agent: Sulfated beta cyclodextrin
Concentration: 115 mg/12 ml saline
Method of Injection: IP
Dosage: 78 mg/kg The hamsters were injected with sulfated beta cyclodextrin 50 minutes before injection of the acetazolamide.

The results of injection of acetazolamide alone are reported in Table 3 as follows; the results of acetazolamide and sulfated beta cyclodextrin are reported in Table 4.

TABLE 3

| Sample No. | Weight of Hamster at Injection (g) | Weight of Hamster After Birth (g) | # Live Fetuses | Defects |
|---|---|---|---|---|
| 1 | 120 | 99 | 8 | 1a, 4b |
| 2 | 124 | 157 | 3 | 1b |
| 3 | 126 | 123 | 5 | 1b |
| 4 | 132 | 93 | Not Pregnant | |
| 5 | 128 | 125 | 4 | 1a, 3b |

Average Number of Fetuses/Litter: 5.0
Average Weight of Mother at Injection: 125 g
Average Weight of Mother After Birth: 126 g
M: 55% (11/20)

TABLE 4

| Sample No. | Weight of Hamster at Injection (g) | Weight of Hamster After Birth (g) | # Live Fetuses | Defects |
|---|---|---|---|---|
| 1 | 120 | 97 | 15 | 2b |
| 2 | 128 | 117 | 10 | 6a, 1b, 1c |
| 3 | 128 | 130 | 6 | 1b |
| 4 | 138 | 102 | 12 | 1b |
| 5 | 118 | 119 | 6 | 1b |

Average Number of Fetuses/Litter: 9.9
Average Weight of Mother at Injection: 126 g
Average Weight of Mother After Birth: 113 g
M*: 27% (13/49)
Blocking Value: 49% (27/55)

EXAMPLE 3

Teratogen: Sodium Arsenic
Concentration: 125 mg/25 ml saline
Method of Injection: IP
Dosage: 25 mg/kg
Blocking Agent: Sulfated beta cyclodextrin
Concentration: 115 mg/12 ml saline
Method of Injection: IP
Dosage: 79 mg/kg The hamsters were injected with sulfated beta cyclodextrin 50 minutes before injection of the sodium arsenic.

The results of injection of sodium arsenic alone are reported in Table 5 as follows; the results of sodium arsenic and sulfated beta cyclodextrin are reported in Table 6.

TABLE 5

| Sample No. | Weight of Hamster at Injection (g) | Weight of Hamster After Birth (g) | # Live Fetuses | Defects |
|---|---|---|---|---|
| 1 | 124 | 118 | Not Pregnant | |
| 2 | 142 | 100 | 7 | 2a, 2b |
| 3 | 126 | 109 | 6 | 1a, 1b |
| 4 | 106 | 123 | 10 | 5a |
| 5 | 128 | 115 | 14 | 3a, 2b |

Average Number of Fetuses/Litter: 9.2
Average Weight of Mother at Injection: 126 g
Average Weight of Mother After Birth: 112 g
M: 43% (16/37)

TABLE 6

| Sample No. | Weight of Hamster at Injection (g) | Weight of Hamster After Birth (g) | # Live Fetuses | Defects |
|---|---|---|---|---|
| 1 | 112 | 111 | 14 | 0 |
| 2 | 112 | 106 | 10 | 5a, 1c |
| 3 | 132 | 116 | 6 | 0 |
| 4 | 126 | 109 | 12 | 1b |
| 5 | 122 | 109 | 6 | 1b |

Average Number of Fetuses/Litter: 9.6
Average Weight of Mother at Injection: 121 g
Average Weight of Mother After Birth: 110 g
M*: 17% (8/48)
Blocking Value: 61% (17/43)

EXAMPLE 4

Teratogen: Sodium Arsenic
Concentration: 125 mg/25 ml saline
Method of Injection: IP
Dosage: 25 mg/kg
Blocking Agent: Sulfated beta cyclodextrin
Concentration: 115 mg/12 ml saline
Method of Injection: IP
Dosage: 80 mg/kg The hamsters were injected with sulfated beta cyclodextrin 50 minutes before injection of the sodium arsenic.

The results of injection of sodium arsenic alone are reported in Table 7 as follows; the results of sodium arsenic and sulfated beta cyclodextrin are reported in Table 8.

TABLE 7

| Sample No. | Weight of Hamster at Injection (g) | Weight of Hamster After Birth (g) | # Live Fetuses | Defects |
|---|---|---|---|---|
| 1 | 125 | 123 | 10 | 4a, 3b |
| 2 | 126 | 121 | 13 | 3a, 2b |
| 3 | 130 | 129 | 9 | 2a, 3b |
| 4 | 122 | 120 | 13 | 2a, 6b |
| 5 | 124 | 126 | 10 | 1a, 9b |

Average Number of Fetuses/Litter: 11.0
Average Weight of Mother at Injection: 125 g
Average Weight of Mother After Birth: 124 g
M: 64% (35/55)

TABLE 8

| Sample No. | Weight of Hamster at Injection (g) | Weight of Hamster After Birth (g) | # Live Fetuses | Defects |
|---|---|---|---|---|
| 1 | 126 | 120 | 8 | 1a |
| 2 | 122 | 122 | 5 | 2a, 2b |
| 3 | 114 | 108 | 10 | 4a, 4b |

TABLE 8-continued

| Sample No. | Weight of Hamster at Injection (g) | Weight of Hamster After Birth (g) | # Live Fetuses | Defects |
|---|---|---|---|---|
| 4 | 124 | 123 | 7 | 1a, 3b |
| 5 | 114 | 121 | 7 | 1a, 1b |

Average Number of Fetuses/Litter: 7.4
Average Weight of Mother at Injection: 120 g
Average Weight of Mother After Birth: 119 g
M*: 51% (19/37)
Blocking Value: 21% (51/64)

EXAMPLE 5

Teratogen: Hydroxy Urea
Concentration: 2000 mg/15 ml saline
Method of Injection: IP
Dosage: 865 mg/kg
Blocking Agent (I): Sulfated beta cyclodextrin
Concentration: 115 mg/12 ml saline
Method of Injection: SC
Dosage: 82 mg/kg
Blocking Agent (II): Sulfated beta cyclodextrin + Naloxone
Concentration: 115 mg/12 ml saline of sulfated beta cyclodextrin + 130 mg./12 ml saline of naloxone
Method of Injection: IP
Dosage: 82 mg/kg sulfated beta cyclodextrin; 50 mg/kg naloxone For the results shown in Table 10, the hamsters were injected with sulfated beta cyclodextrin 50 minutes before injection of the hydroxy urea. For the results shown in Table 11, the hamsters were injected with sulfated beta cyclodextrin/naloxone about 50 minutes before injection of the hydroxy urea.

The results of injection of hydroxy urea alone are reported in Table 9 as follows; the results of hydroxy urea and sulfated beta cyclodextrin are reported in Table 10; and the results of the hydroxy urea and sulfated beta cyclodextrin/naloxone are reported in Table 11.

TABLE 9

| Sample No. | Weight of Hamster at Injection (g) | Weight of Hamster After Birth (g) | # Live Fetuses | Defects |
|---|---|---|---|---|
| 1 | 118 | 115 | None - all resorbed | |
| 2 | 102 | 105 | None - all resorbed | |
| 3 | 124 | 122 | None - all resorbed | |
| 4 | 114 | 115 | 1 | 1bfd |
| 5 | 108 | 109 | None - all resorbed | |
| 6 | 100 | 112 | Not Pregnant | |
| 7 | 90 | 105 | Not Pregnant | |

Average Number of Fetuses/Litter: 1
Average Weight of Mother at Injection: 113 g
Average Weight of Mother After Birth: 115 g (only hamster #4)
M: 100% (1/1)

TABLE 10

| Sample No. | Weight of Hamster at Injection (g) | Weight of Hamster After Birth (g) | # Live Fetuses | Defects |
|---|---|---|---|---|
| 1 | 134 | Died | — | — |
| 2 | 114 | 117 | Not Pregnant | |
| 3 | 112 | 124 | 2 | 2bfd |
| 4 | 116 | 126 | 2 | 2bfd |

TABLE 10-continued

| Sample No. | Weight of Hamster at Injection (g) | Weight of Hamster After Birth (g) | # Live Fetuses | Defects |
|---|---|---|---|---|
| 5 | 122 | 124 | 2 | 2bfd |

Average Number of Fetuses/Litter: 2.0
Average Weight of Mother at Injection: 117 g
Average Weight of Mother After Birth: 125 g
M*: 100% (6/6)
Blocking Value: 0% (100/100) Blocking effect was indicated by increased number of fetuses/litter and increase in average fetus size.

TABLE 11

| Sample No. | Weight of Hamster at Injection (g) | Weight of Hamster After Birth (g) | # Live Fetuses | Defects |
|---|---|---|---|---|
| 1 | 122 | 129 | None - all resorbed | |
| 2 | 106 | 113 | 1 | 1bfd |
| 3 | 144 | Dead (due to puncture of blood vessel) | | |
| 4 | 112 | 113 | 5 | 1bg, 1b |
| 5 | 112 | 113 | None - all resorbed | |

Average Number of Fetuses/Litter: 3.0
Average Weight of Mother at Injection: 109 g
Average Weight of Mother After Birth: 113 g
M*: 50% (3/6)
Blocking Value: 50% (50/100)

EXAMPLE 6

Teratogen: Hydroxy Urea
Concentration: 2000 mg/15 ml saline
Method of Injection: SC
Dosage: 835 mg/kg
Blocking Agent: Sulfated beta cyclodextrin
Concentration: 145 mg/15 ml saline
Method of Injection: IP
Dosage: 40 mg/kg The hamsters were injected with sulfated beta cyclodextrin 50 minutes before injection of the hydroxy urea.

The results of injection of hydroxy urea alone are reported in Table 12 as follows; the results of hydroxy urea and sulfated beta cyclodextrin are reported in Table 13.

TABLE 12

| Sample No. | Weight of Hamster at Injection (g) | Weight of Hamster After Birth (g) | # Live Fetuses | Defects |
|---|---|---|---|---|
| 1 | 118 | 125 | 2 | 1bdfg, 1g |
| 2 | 120 | 120 | 7 | 5bdfg, 1g |
| 3 | 112 | 120 | 1 | 1bdfg |
| 4 | 118 | 127 | 2 | 2bdfg |
| 5 | 120 | 125 | 3 | 3bdfg |

Average Number of Fetuses/Litter: 3.0
Average Weight of Mother at Injection: 118 g
Average Weight of Mother After Birth: 123 g
M: 93% (14/15)

TABLE 13

| Sample No. | Weight of Hamster at Injection (g) | Weight of Hamster After Birth (g) | # Live Fetuses | Defects |
|---|---|---|---|---|
| 1 | 126 | 124 | 2 | 2dfb |
| 2 | 126 | Died | — | — |
| 3 | 116 | 132 | None - all resorbed | |
| 4 | 120 | 127 | 1 | 1dfb |

TABLE 13-continued

| Sample No. | Weight of Hamster at Injection (g) | Weight of Hamster After Birth (g) | # Live Fetuses | Defects |
|---|---|---|---|---|
| 5 | 114 | 123 | 4 | 1f |

Average Number of Fetuses/Litter: 2.3
Average Weight of Mother at Injection: 120 g
Average Weight of Mother After Birth: 125 g
M*: 57% (4/7)
Blocking Value: 39% (57/93)

EXAMPLE 7

Teratogen: Hydroxy Urea
Concentration: 2000 mg/15 ml saline
Method of Injection: SC
Dosage 800 mg/kg
Blocking Agent: Sulfated beta cyclodextrin
Concentration: 145 mg/15 ml saline
Method of Injection: SC
Dosage: 37 mg/kg The hamsters were injected with sulfated beta cyclodextrin 50 minutes before injection of the hydroxy urea.

The results of injection of hydroxy urea alone are reported in Table 14 as follows; the results of hydroxy urea and sulfated beta cyclodextrin are reported in Table 15.

TABLE 14

| Sample No. | Weight of Hamster at Injection (g) | Weight of Hamster After Birth (g) | # Live Fetuses | Defects |
|---|---|---|---|---|
| 1 | 126 | 127 | 2 | 2df |
| 2 | 120 | 117 | Not Pregnant | |
| 3 | 132 | 135 | None - all resorbed | |
| 4 | 120 | 138 | 6 | 1f, 3df |
| 5 | 132 | 132 | 6 | 0 |
| 6 | 132 | 138 | None - all resorbed | |

Average Number of Fetuses/Litter: 4.7
Average Weight of Mother at Injection: 126 g
Average Weight of Mother After Birth: 132 g
M: 43% (6/14)

TABLE 15

| Sample No. | Weight of Hamster at Injection (g) | Weight of Hamster After Birth (g) | # Live Fetuses | Defects |
|---|---|---|---|---|
| 1 | 142 | 134 | 9 | 2a, 3d, 1bfd |
| 2 | 124 | 122 | 8 | 4f |
| 3 | 126 | 131 | 2 | 2f |
| 4 | 132 | 130 | 11 | 0 |
| 5 | 128 | 132 | 3 | 1df, 1f |

Average Number of Fetuses/Litter: 6.7
Average Weight of Mother at Injection: 130 g
Average Weight of Mother After Birth: 130 g
M*: 43% (14/33)
Blocking Value: 0%
There is no block of the percent fetuses defective, but there is less litter resorption; there are more fetuses/litter; there is a decreased number of spina bifida fetuses; and there is less gastroschisis

EXAMPLE 8

Teratogen: Ethyl Alcohol
Concentration: 100% C.P. grade ethanol
Method of Injection: SC
Dosage: 1080 mg/kg
Blocking Agent: Sulfated beta cyclodextrin
Concentration: 145 mg/15 ml saline
Method of Injection: SC Dosage: 36 mg/kg The hamsters were injected with sulfated beta cyclodextrin 50 minutes before injection of the ethyl alcohol.

The results of injection of ethyl alcohol alone are reported in Table 16 as follows; the results of ethyl alcohol and sulfated beta cyclodextrin are reported in Table 17.

TABLE 16

| Sample No. | Weight of Hamster at Injection (g) | Weight of Hamster After Birth (g) | # Live Fetuses | Defects |
|---|---|---|---|---|
| 1 | 142 | 140 | 3 | 3a |
| 2 | 128 | 122 | 9 | 8a |
| 3 | 120 | 126 | None - all resorbed | |
| 4 | 124 | 126 | None - all resorbed | |
| 5 | 138 | 135 | 1 | 1cd |
| 6 | 130 | 114 | 12 | 0 |
| 7 | 130 | 133 | 2 | 1ae, 1a |
| 8 | 130 | 124 | 2 | 1ae, 1a |
| 9 | 142 | 142 | 6 | 6a |
| 10 | 120 | 112 | 12 | 10a, 1d |
| 11 | 128 | 136 | None - all resorbed | |

Average Number of Fetuses/Litter: 5.9
Average Weight of Mother at Injection: 133 g
Average Weight of Mother After Birth: 128 g
M: 70% (33/47)
Blocking also indicated by decreased litter resorption; increased number of fetuses/litter; larger fetuses in litter, decrease in exencephaly defects and blocking of spina bifida defects

TABLE 17

| Sample No. | Weight of Hamster at Injection (g) | Weight of Hamster After Birth (g) | # Live Fetuses | Defects |
|---|---|---|---|---|
| 1 | 108 | Died | — | — |
| 2 | 120 | 122 | 11 | 2a, 2b |
| 3 | 136 | 125 | 12 | 4a, 2b |
| 4 | 126 | 133 | 3 | 2a, 1b |
| 5 | 150 | 141 | 5 | 3a, 2g |
| 6 | 138 | 134 | 1 | 1a |
| 7 | 118 | 126 | 9 | 2a, 2b |
| 8 | 134 | 126 | 1 | 1g |
| 9 | 124 | 121 | 10 | 4a, 4b |
| 10 | 142 | 134 | 12 | 1a, 3b |
| 11 | 134 | 130 | 9 | 1a, 2b |

Average Number of Fetuses/Litter: 7.3
Average Weight of Mother at Injection: 132 g
Average Weight of Mother After Birth: 129 g
M*: 53% (39/73)
Blocking Value: 24% (53/70)
Blocking effect indicated by decreased litter resorption; increased number of fetuses/litter; larger fetuses in litter; decrease in exencephaly defects; no spina bifida defects

EXAMPLE 9

Teratogen: Acetazolamide
Concentration: 4500 mg/30 ml saline/CMC
Method of Injection: IP
Dosage: 1365 mg/kg
Blocking Agent: Sulfated beta cyclodextrin
Concentration: 60 mg/6 ml saline
Method of Injection: SC
Dosage: 35 mg/kg The hamsters were injected with sulfated beta cyclodextrin 30–45 minutes after injection of the acetazolamide.

The results of injection of acetazolamide alone are reported in Table 18 as follows; the results of acetazolamide and sulfated beta cyclodextrin are reported in Table 19.

TABLE 18

| Sample No. | Weight of Hamster at Injection (g) | Weight of Hamster After Birth (g) | # Live Fetuses | Defects |
|---|---|---|---|---|
| 1 | 132 | 128 | 10 | 2b |
| 2 | 130 | 118 | 6 | 2a, 1b |
| 3 | 124 | 112 | 8 | 1a, 2b |
| 4 | 132 | 115 | 11 | 1a, 4b |
| 5 | 138 | 134 | 9 | 5a, 3b, 1g |
| 6 | 134 | 99 | 10 | 5a, 2b, 3g |

Average Number of Fetuses/Litter: 9.0
Average Weight of Mother at Injection: 132 g
Average Weight of Mother After Birth: 118 g
M: 59% (32/54)

TABLE 19

| Sample No. | Weight of Hamster at Injection (g) | Weight of Hamster After Birth (g) | # Live Fetuses | Defects |
|---|---|---|---|---|
| 1 | 150 | 136 | 12 | 0 |
| 2 | 130 | 122 | 4 | 2b |
| 3 | 138 | 132 | 12 | 5b |
| 4 | 140 | 127 | 6 | 0 |
| 5 | 128 | 122 | 8 | 1b |
| 6 | 126 | 123 | Not Pregnant | |

Average Number of Fetuses/Litter: 8.4
Average Weight of Mother at Injection: 137 g
Average Weight of Mother After Birth: 128 g
M*: 19% (8/42)
Blocking Value: 68% (19/59)

EXAMPLE 10

Teratogen: Arsenic
Concentration: 125 mg/25 ml saline
Method of Injection: IP
Dosage: 26.5 mg/kg
Blocking Agent: Sulfated beta cyclodextrin
Concentration: 145mg/15 ml saline
Method of Injection: SC
Dosage: 37 mg/kg The hamsters were injected with sulfated beta cyclodextrin about 20 minutes after injection of the arsenic.

The results of injection of arsenic alone are reported in Table 20 as follows; the results of arsenic and sulfated beta cyclodextrin are reported in Table 21.

TABLE 20

| Sample No. | Weight of Hamster at Injection (g) | Weight of Hamster After Birth (g) | # Live Fetuses | Defects |
|---|---|---|---|---|
| 1 | 132 | 132 | 8 | 2a, 4b |
| 2 | 124 | 117 | 11 | 1a, 5b |
| 3 | 132 | 127 | 12 | 4a, 6b |
| 4 | 118 | 125 | 7 | 5a, 1b |
| 5 | 142 | 123 | 11 | 3a, 6b |

Average Number of Fetuses/Litter: 9.8
Average Weight of Mother at Injection: 129 g
Average Weight of Mother After Birth: 125 g
M: 76% (37/49)

TABLE 21

| Sample No. | Weight of Hamster at Injection (g) | Weight of Hamster After Birth (g) | # Live Fetuses | Defects |
|---|---|---|---|---|
| 1 | 134 | 135 | None - all resorbed | |
| 2 | 126 | 130 | 9 | 2b, 1g |
| 3 | 124 | 120 | 11 | 1a, 3b |
| 4 | 136 | 124 | 14 | 1a, 2b. 1 dead |

TABLE 21-continued

| Sample No. | Weight of Hamster at Injection (g) | Weight of Hamster After Birth (g) | # Live Fetuses | Defects |
|---|---|---|---|---|
| 5 | 136 | 141 | 7 | 3 |

Average Number of Fetuses/Litter: 10.2
Average Weight of Mother at Injection: 131 g
Average Weight of Mother After Birth: 129 g
M*: 34% (14/41)
Blocking Value: 55% (34/76)

EXAMPLE 11

This example illustrates the effect of heat (hyperthermia) as the teratogen. The procedure of the previous examples was followed. A dosage of 50 mg/kg of sulfated beta cyclodextrin was injected IP in the hamsters about 20 minutes before exposure to heat. After injection, the hamsters were placed in a climate controlled box at 42° C. for 1 hour. Air was supplied to the box and the humidity of the air was about 50-60%.

The results of exposure to the increased heat alone are reported in Table 22 as follows; the results of increased heat and sulfated beta cyclodextrin are reported in Table 23.

TABLE 22

| Sample No. | Weight of Hamster at Injection (g) | Weight of Hamster After Birth (g) | # Live Fetuses | Defects |
|---|---|---|---|---|
| 1 | 133 | 130 | 8 | 1a, 3b, 3h |
| 2 | 140 | 138 | 11 | 4h |
| 3 | 126 | 124 | 12 | 2a, 2b, 1c |
| 4 | 131 | 130 | 8 | 2a, 1b, 3h |
| 5 | 130 | 125 | 6 | 3h, 1b |
| 6 | 135 | 131 | 2 | 1h, 1b |
| 7 | 129 | 126 | 6 | 2h, 1a, 1b |

Average Number of Fetuses/Litter: 7.6
Average Weight of Mother at Injection: 132 g
Average Weight of Mother After Birth: 129 g
M: 60% (32/53)

TABLE 23

| Sample No. | Weight of Hamster at Injection (g) | Weight of Hamster After Birth (g) | # Live Fetuses | Defects |
|---|---|---|---|---|
| 1 | 135 | 136 | 9 | 2b |
| 2 | 131 | 130 | 11 | 1b |
| 3 | 128 | 129 | 11 | 4b |
| 4 | 135 | 135 | 10 | 1a |
| 5 | 140 | 139 | 11 | 1a |
| 6 | 142 | 135 | 12 | 3b |
| 7 | 138 | 137 | 10 | 3b |

Average Number of Fetuses/Litter: 10.6
Average Weight of Mother at Injection: 136 g
Average Weight of Mother After Birth: 134 g
M*: 20% (15/74)
Blocking Value: 67% (20/60)

GENERAL DISCUSSION OF EXAMPLES

It is apparent from the foregoing examples that the sulfated cyclodextrin, when used in accordance with the present invention, is effective as a blocking agent against a range of teratogens. Both its prophylactic and therapeutic effects are demonstrated.

During the running of the examples it was generally observed that all teratogenic fetuses weigh approximately 10-20% less than control fetuses on average and that the blocked group fetuses weigh intermediately between control and teratogen treated. In other words, blocking with sulfated cyclodextrin not only reduces gross anatomical defects, but also blocks to some degree low birth weight associated with teratogens.

It will be understood that the claims are intended to cover all changes and modifications of the preferred embodiments of the invention herein chosen for the purpose of illustration which do not constitute a departure from the spirit and scope of the invention.

I claim:

1. A method for reducing or blocking the effect of a teratogen on a host in need of such treatment comprising treating said host with an amount of a sulfated cyclodextrin effective to reduce or block the effect of a teratogen on the host in a pharmaceutically acceptable carrier.

2. The method of claim 1 wherein said cyclodextrin is beta cyclodextrin.

3. The method of claim 1 wherein said host is treated with said cyclodextrin before exposure to said teratogen.

4. The method of claim 1 wherein said host is treated with said cyclodextrin after exposure to said teratogen.

5. A method for reducing or blocking the effect of a teratogen on a host that is pregnant with a fetus and is in need of such treatment, thereby preventing or reducing congenital birth defects, said method comprising treating said host with an amount of sulfated cyclodextrin effective to reduce or block the effect of the teratogen on the fetus thereby preventing or blocking a congenital birth defect caused by said teratogen.

6. The method of claim 5 wherein the amount of sulfated cyclodextrin administered per day is between about 5 to about 200 mg/kg of host.

7. The method of claim 5 wherein the amount of sulfated cyclodextrin administered per day is between about 50 to about 90 mg/kg of host.

8. The method of claim 5 wherein the teratogen is selected from the group consisting of acetazolamide, sodium arsenic, arsenic, hydroxy urea, ethyl alcohol and heat.

9. The method of claim 6 wherein the teratogen is selected from the group consisting of acetazolamide, sodium arsenic, arsenic, hydroxy urea, ethyl alcohol and heat.

10. The method of claim 7 wherein the teratogen is selected from the group consisting of acetazolamide, sodium arsenic, arsenic, hydroxy urea, ethyl alcohol and heat.

* * * * *